United States Patent [19]

Kowalski et al.

[11] Patent Number: 4,648,389

[45] Date of Patent: Mar. 10, 1987

[54] PATIENT TREATMENT TABLE

[75] Inventors: Frank P. Kowalski, Des Plaines; Gerald R. Scott, Elmhurst, both of Ill.

[73] Assignee: Standex International Corporation, Salem, N.H.

[21] Appl. No.: 739,988

[22] Filed: May 31, 1985

[51] Int. Cl.[4] .......... A61F 5/00

[52] U.S. Cl. .......... 128/70; 269/323; 269/325

[58] Field of Search .......... 269/322, 323, 324, 325, 269/326; 128/70, 72, 73, 74

[56] References Cited

U.S. PATENT DOCUMENTS

| | | | |
|---|---|---|---|
| 2,381,922 | 8/1945 | Norris | 128/73 |
| 4,142,520 | 3/1979 | Herbold | 269/325 |
| 4,271,830 | 6/1981 | Moon | 269/323 |
| 4,401,110 | 8/1983 | Ekholm | 128/70 |

*Primary Examiner*—Frederick R. Schmidt
*Assistant Examiner*—Judy J. Hartman
*Attorney, Agent, or Firm*—Mason, Kolehmainen, Rathburn & Wyss

[57] ABSTRACT

A patient treatment table includes a base and a patient supporting table mounted for pivotal movement relative to the base between a first generally horizontal position supporting a patient at a convenient level for treatment and a second generally upstanding position for facilitating a patient in mounting and dismounting. The table includes a footboard at the foot end of the table which is positioned in a generally horizontal position near the surface of the floor, to assist a patient in mounting and dismounting, when the table is in the upstanding position. A linkage mechanism is provided for interconnecting the table and the footboard so that as the table is moved between the upstanding and horizontal positions the footboard is automatically moved to a tucked away position beneath the amnle supporting cushion of the table so that the chiropractor can stand relatively close to the feet of the patient and can make the numerous checks on the relative alignment of the patient's feet, which are required during each chiropractic treatment, without producing back strain or other physical impairment of the chiropractor at the end of the day.

15 Claims, 5 Drawing Figures

FIG. 1
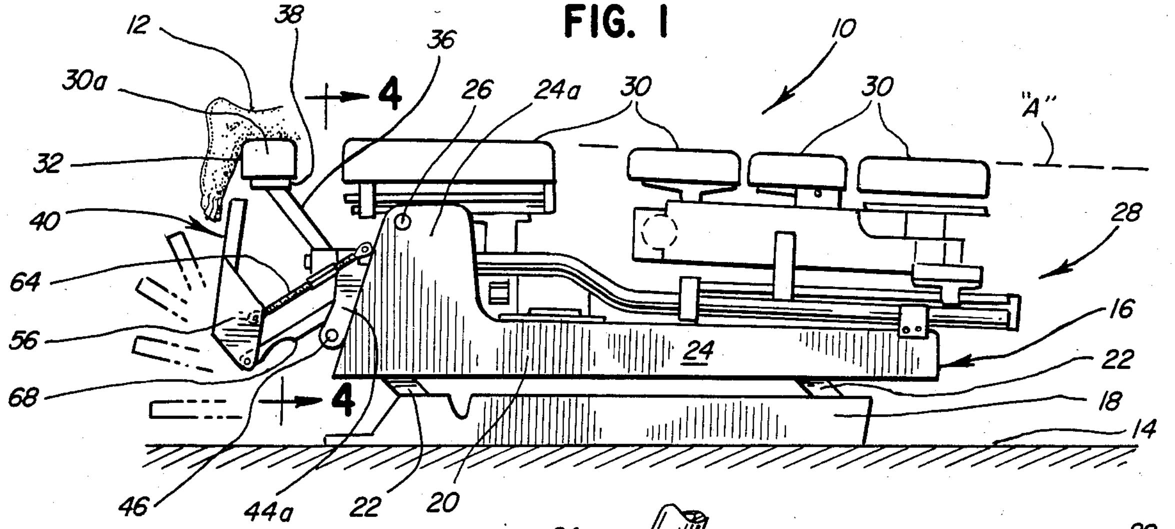
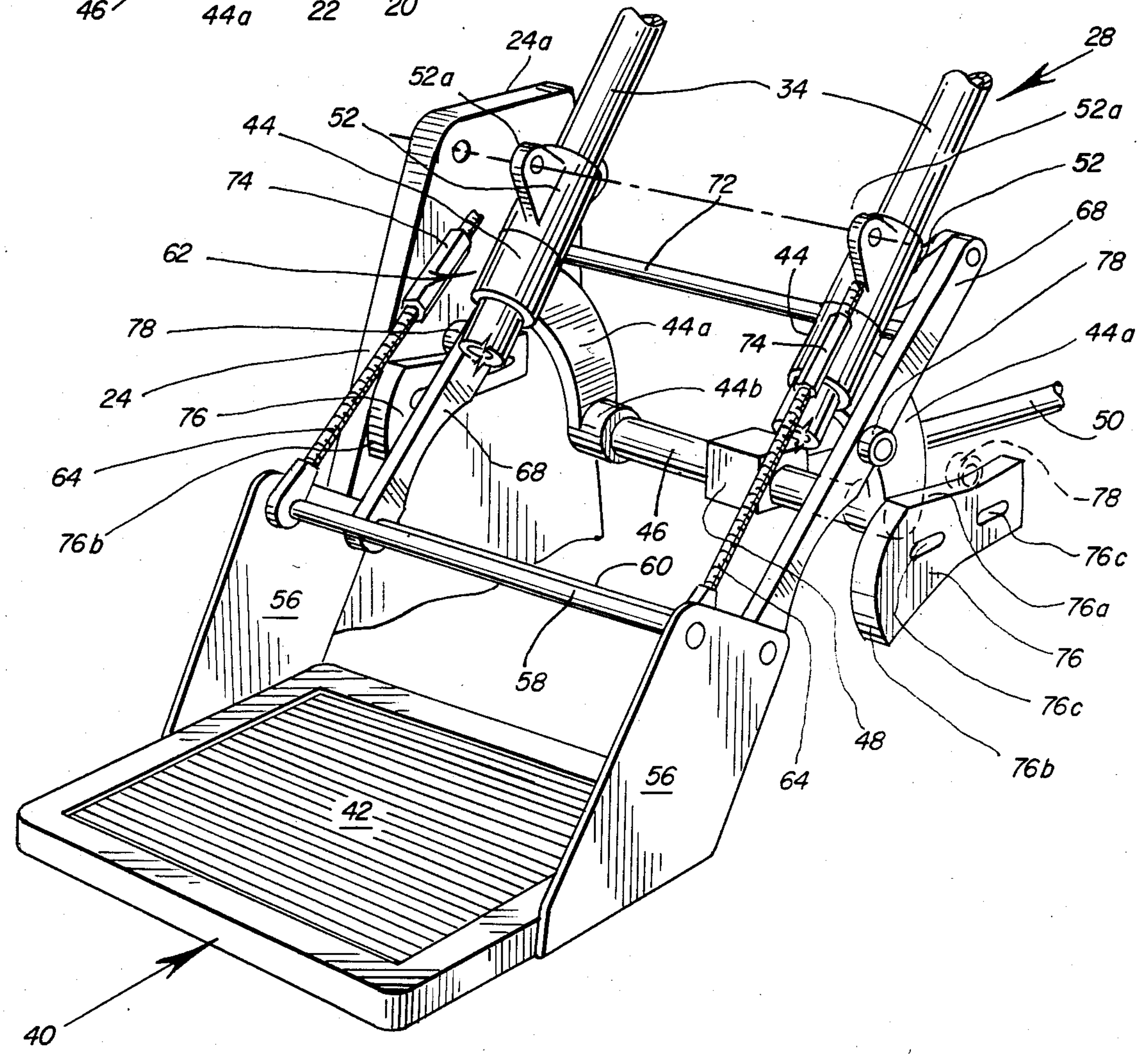
FIG. 2

PATIENT TREATMENT TABLE

BACKGROUND OF THE INVENTION

1. Field of the Invention

The present invention relates generally to a new and improved patient treatment table and more particularly to an improved patient treatment table which is particularly well suited for chiropractic adjustments on a patient lying on the table.

More particularly, the patient treatment table of the present invention is of the type wherein the patient supporting table is movable between a generally horizontal position for treatment of the patient at a convenient working level for the chiropractor and an upstanding position to aid the patient in mounting and dismounting from the table.

2. Description of the Prior Art

U.S. Pat. No. 4,401,110 discloses a patient treatment table having a footboard for supporting a patient in a standing position during mounting and dismounting from the table when the table is tilted upwardly to a position near the vertical. As shown in FIG. 1 of the aforementioned patent the footboard is positioned a substantial distance beyond the patient's feet when the table is in a horizontal position so that the chiropractor must bend his back and reach over the rearwardly extending footboard to make the numerous checks on the relative alignment of the patient's feet which are required during each chiropractic treatment. As a result, the chiropractor may experience back pain or other physical ailments at the end of a day involving many such chiropractic treatments.

OBJECTS OF THE PRESENT INVENTION

It is an object of the present invention to provide a new and improved patient treatment table which avoids the above described disadvantages of prior art arrangements.

It is another object of the present invention to provide a new and improved patient treatment table having a footboard which is automatically moved to a tucked away position beneath the ankle supporting cushion of the table when the table is moved to a horizontal position so that the chiropractor can stand close to the foot end of the table during the chiropractic treatment.

It is further object of the present invention is to provide a new and improved patient treatment table having an automatically adjusted foot board of the character described wherein as the table is pivoted upwardly from the horizontal position with a patient thereon the foot board automatically extends outwardly to accept the weight of a patient as the patient approaches an upright position ready to dismount from the table.

SUMMARY OF THE INVENTION

The foregoing and other objects and advantages of the present invention are accomplished in a new and improved patient treatment table which includes a base adapted to be supported from a floor surface and having a patient supporting table structure mounted for pivotal movement relative to the base between a generally horizontal position for supporting the patient at a convenient working level during treatment to an upstanding position which facilitates mounting and dismounting from the table. The patient treatment table includes an automatically controlled footboard adjacent the foot end of the table which is initially positioned in a generally horizontal, outwardly extending position near the floor level for supporting the patient in a standing position during mounting and dismounting from the table. As the table pivots to a horizontal position, the footboard is retracted and tucked away into a generally vertical position below and close to the foot end of the table. The footboard is fully tucked away as the table reaches the horizontal position at which the full weight of the patient lying thereon is accepted. After treatment has been completed, the table is elevated from the horizontal position towards an upstanding position to facilitate a patient in mounting or dismounting, and the footboard automatically begins to project outwardly as the table tilts up in order to accept the feet and weight of the patient so that as the table reaches a maximum upstanding position the patient is in a generally standing position, fully supported on the foot board and can then step off easily onto the floor surface.

BRIEF DESCRIPTION OF THE DRAWINGS

For a better understanding of the present invention, reference should be had to the following detailed description taken in conjunction with the drawings, in which:

FIG. 1 is a side elevational view of a new and improved patient treatment table in accordance with the features of present invention and shown in a horizontal position ready for treatment of a patient lying thereon with the footboard in a tucked away configuration;

FIG. 2 is an enlarged, fragmentary, exploded, foot end perspective view of the footboard assembly of the table of FIG. 1 shown as it appears when the table is in an upwardly extending position with the foot board in a generally horizontal position close to the floor level ready to accept the weight of a patient standing thereon;

DETAILED DESCRIPTION OF A PREFERRED EMBODIMEWNT

Figure 3A:
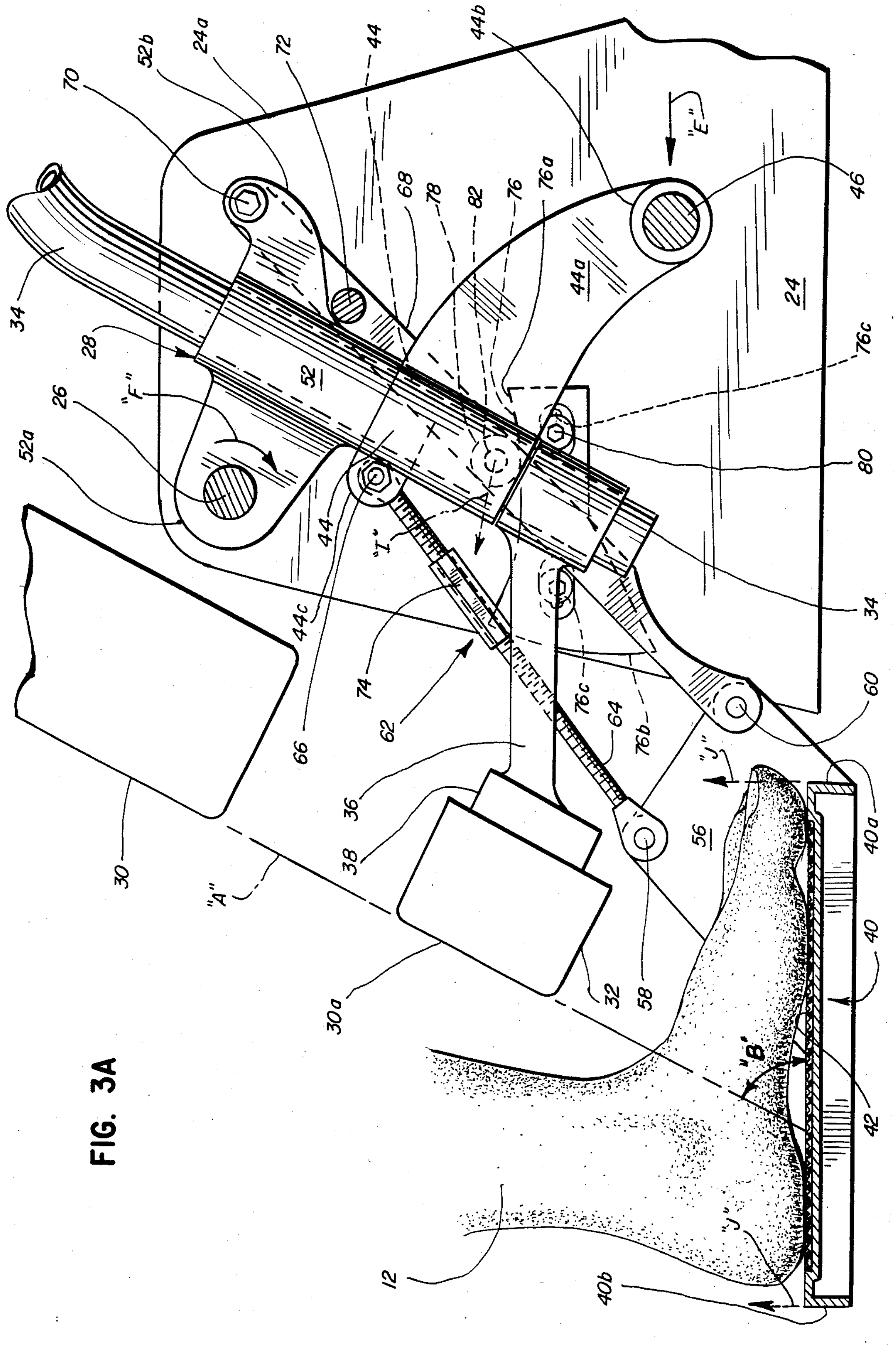
FIG. 3A is an enlarged, fragmentary, elevational cross sectional view taken along a longitudinal, central axis of the patient treatment table and illustrating the foot board in a generally horizontal position for accomodating a patient standing on the footboard during mounting or dismounting.

Referring now more particularly to the drawings, therein is illustrated a new and improved patient treatment table characterized in accordance with the present invention and referred to generally in FIG. 1 by the reference numeral 10. The patient treatment table 10 is adapted to support a patient 12 lying in a generally horizontal or prone position at a convenient working level above a floor surface 14 in order to facilitate treatment by the chiropractor.

The table 10 is an improvement on a table of the type shown in U.S. Pat. No. 4,401,110, issued Aug. 30, 1983 and assigned to the same assignee of the present application, and includes a base structure 16 having a lower base 18 adapted to rest on the floor surface 14 and an upper base 20 which is movable up and down relative thereto as more fully described in the aforementioned patent. The upper and lower bases are interconnected by pivot links 22 in order to provide an adjustment in working level for the chiropractor.

The upper base 20 includes a pair of side frame plate members 24 interconnected by transverse cross members (not shown) which provide a strong rigid upper base frame. Each side frame plate 24 includes an upstanding end portion 24a at the foot end of the base structure, and these upstanding side frame portions provide bearings for the opposite ends of a pivot axle 26. The axle 26 pivotally interconnects a foot end of an upper table frame structure 28 which provides support for a plurality of spaced apart, table cushions 30 on which a patient 12 lies while being treated. The individual cushions 30 are adjustable relative to one another in order to accommodate patients of different size and shape, and a relatively small ankle cushion 30a at the foot end of the table structure provides support for a patient's ankles while the patient is lying in prone position on the table cushions.

The ankle cushion 30a includes an outer end surface 32 forming the foot end of the table and is supported from foot end portions of a pair of elongated side frame support rods 34 which are interconnected together by transverse cross members (nto shown) provided at intervals along the length thereof. The ankle cushion 30a is supported from the frame rods 34 on brackets 36 which are interconnected at their outer ends by a cross member 38 which provides a direct support base for the ankle cushion.

In accordance with the present invention, the table 10 includes an automatically controlled foot board 40 having a pad 42 on the upper surface to provide a nonskid traction surface for the feet of a patient while standing thereon as shown in FIG. 3A. The foot board is in a generally horizontal position, closely adjacent the floor surface 14 when the table frame structure 28 is in an upwardly extended, tilted position as shown in FIG. 3A for convience of a patient while mounting and dismounting. In this position the foot board extends outwardly of and intersects a plane "A" which is generally coincident with the upper surface of the patient support cushions 30 on the table frame. As illustrated in FIG. 3A, the plane "A" extends upwardly at a relatively large angle "B" with respect to the surface of the foot pad 42 and an open space is provided between the end surface 32 of the ankle cushion 30a and the upper surface of the foot pad 42 above the footboard 40 to accommodate the forward portion of the feet of the patient while standing on the generally horizontal footboard.

Figure 3B:
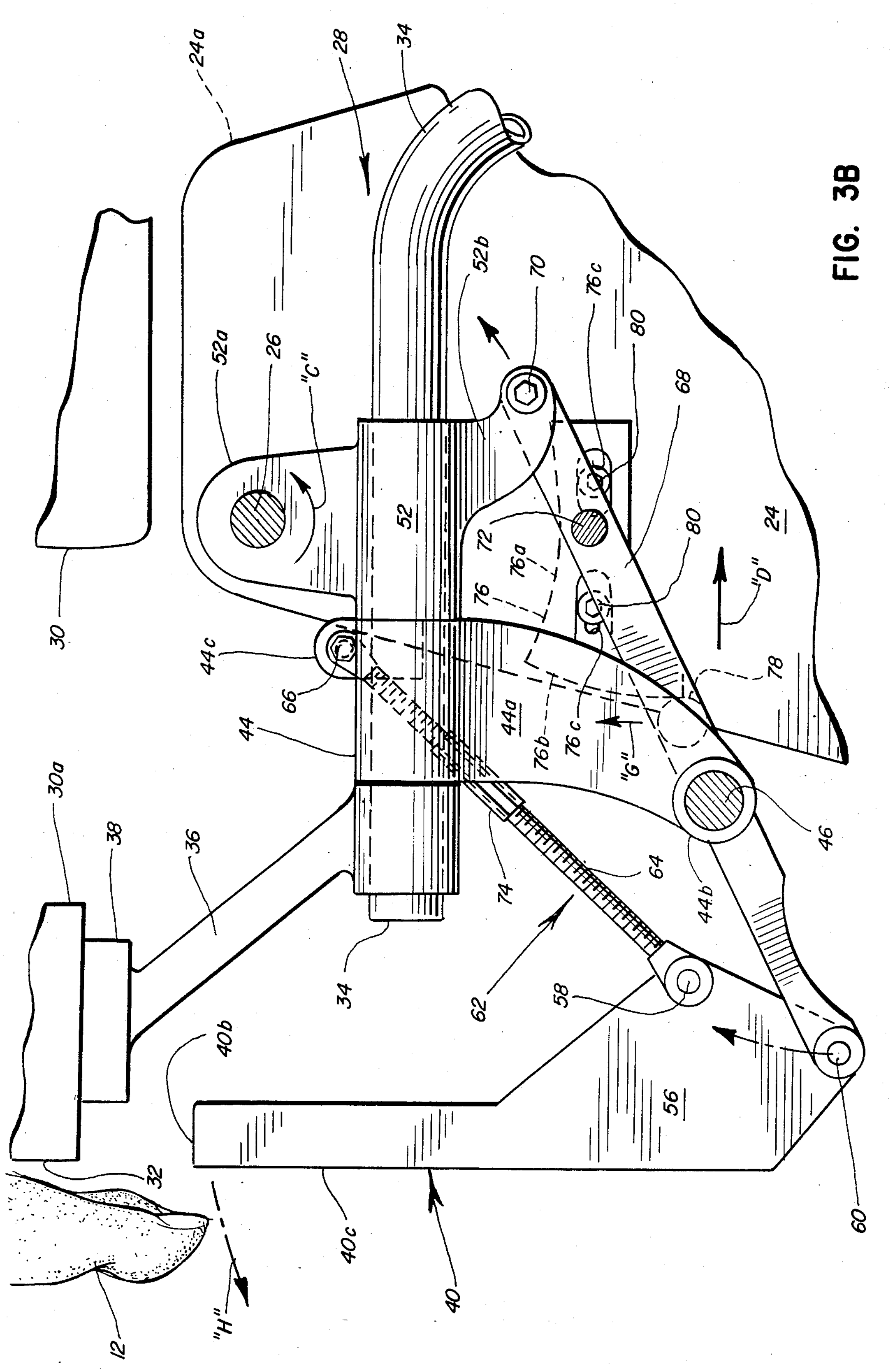
FIG. 3B is a fragmentary, sectional elevational view similar to FIG. 3A but illustrating the foot board in a tucked away position underneath the foot end of the table while the table is supporting a patient thereon in a generally horizontal position for treatment.

Referring to FIG. 3A, as the table frame 28 pivots downwardly in a clockwise direction (arrow F) about the support axle 26 from the upstanding position toward to a patient supporting, generally horizontal position, as shown in FIGS. 1 and 3B, the footboard 40 pivots from the horizontal position of FIG. 3A in a clockwise direction about an inner end 40a to a substantially vertically extending, tuck-away position as shown in FIG. 3B wherein an outer end 40b of the footboard is spaced below the ankle cushion 30a as shown in FIG. 3B. In this tuck-away position as illustrated in FIGS. 1 and 3B, an underside 40c of the footboard is aligned in a generally vertical arrangement with the end surface 32 of the table cushion 30A so that the chiropractor can stand closely adjacent the foot end of the table structure and does not have to bend over and reach out to grasp the patient's feet when making the numerous checks on relative foot alignment of the patient during a chiropractic treatment.

At the foot end of the table frame structure, the side frame rods 34 are interconnected by structure comprising sleeves 44 mounted on the side frame members and having downwardly depending, curved arms 44a formed with cylindrical hollow bosses 44b at the lower end thereof on the inner faces of the arms for receiving opposite end portions of a transversely extending axle or cross member 46. At a mid point on the axle 46, there is provided a thrust block 48 to which is connected the outer end of a piston rod 50 of a hydraulic cylinder provided for pivoting the table frame 28 relative to the upper base 20 as more fully described in the aforementioned patent.

The table frame 20 is supported for pivotal movement relative to the upper base 20 on the axle 26 with sleeves 52 which are mounted on the rod-form side frame members 34 adjacent and inwardly of the sleeves 44. Each sleeve 52 is provided with an upwardly extending arm or bracket 52a having an aperture and journalled on the axle 26 and the brackets are interconnected by a transversely extending hollow sleeve 54 also journalled on the pivot support axle 26. The foot end portion of the table frame 28 is thus supported from the pivot axle 26 carried by the upper base 20 and at a level below the axle. The frame is pivotally moveable between a generally horizontal position as shown in FIGS. 1 and 3B in a counterclockwise direction (arrow "C") toward a generally upstanding, tilted position as shown in FIG. 3a. Pivot control is provided by the application of pulling force as represented by the arrow "D" in FIG. 3B exerted by retraction of the piston rod 50 into the hydraulic cylinder. Outward extension of the piston rod exerts a force as represented by the arrow "E" in FIG. 3A resulting in clockwise pivotal movement of the table frame 28 as indicated by the arrow "F". As the table pivots from the upstanding, tilted position therein shown toward the horizontal position shown in FIGS. 1 and 3B.

In accordance with the present invention, the tuck-away footboard 40 is provided with a pair of upstanding side plates 56 on opposite side edges and the upper corners of these side plates are interconnected by a pair of transversely extending rod-like cross members 58 and 60 to form a relatively strong and rigid support for the foot board 40. The foot board is linked to the table and base in order to move as previously described in automatic response to the pivotal movement of the table frame 28 relative to the base structure 16. For this purpose, a linkage mechanism generally indicated by the reference numeral 62 is provided. The linkage mechanism includes a pair of upper adjustable connector links 64 having lower ends pivotally interconnected to the upper connector rod 58 and upper ends pivotally interconnected to upwardly extending ears 44c provided on the sleeves 44 as illustrated best in FIGS. 3A, 3B and 4. The upper end of each upper connecting link 64 is pivotally secured to an upstanding ear 44c by a cap screw assembly 66 which provides a pivotal mount for the upper end of the upper link.

Figure 4:
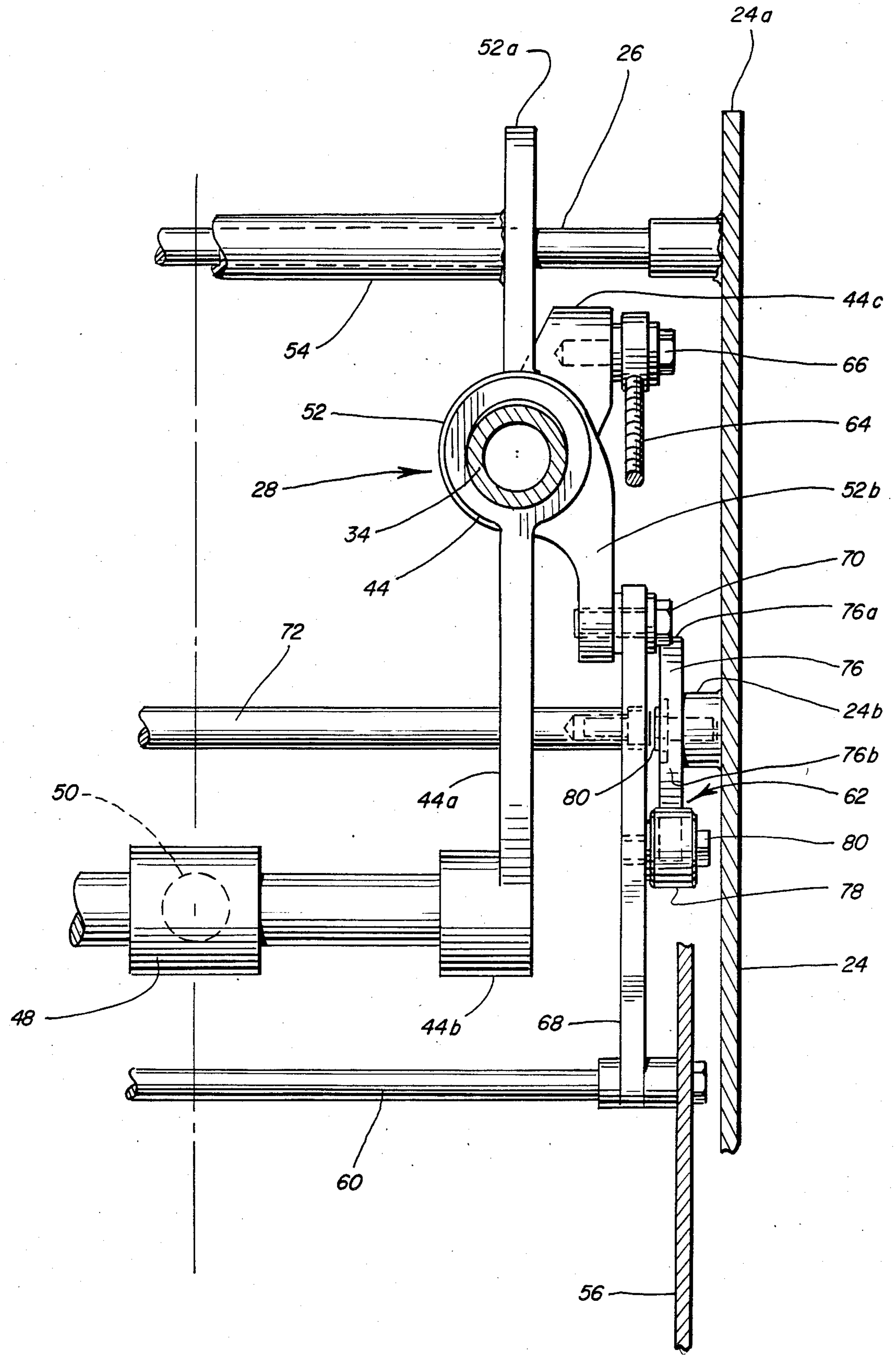
FIG. 4 is a fragmentary, transverse, cross sectional view taken along line 4—4 of FIG. 1.

The linkage assembly further includes a pair of lower links 68, each link having a lower end pivotally interconnected to the lower, transverse connecting rod 60 extending between the foot board side plates 56. Each lower link 68 includes an upper end pivotally interconnected to a downwardly projecting ear 52b provided on an upper sleeve 52 mounted on a respective side frame rod member 34. Pivotal interconnection between the upper ends of the lower links 68 and the ears 52b is provided by cap screw assemblies 70 as best shown in FIGS. 3A, 3B and 4. It will thus be seen that the upper and lower links provide a positive mechanical interconnection between the footboard 40 and the table frame structure 28. Mid-portions of the lower links 68 are also interconnected by a transversely extending connector rod 72 which provides additional strength for the innerconnecting linkage mechanism 62.

As previously indicated, the upper connecting links 64 are adjustable in length and include turnbuckle adjustment sections 74 which provide for precise leveling and alignment of the footboard 40 as desired in relation to the table frame 28. By adjusting the length of the upper connecting links 64, using the turnbuckles 74, the footboard 40 can be brought into precisely level alignment as shown in FIG. 2 and 3A when the table frame 20 is in a maximum angle, upstanding position.

In accordance with the present invention, relative pivotal movement between the pairs of upper and lower links 64 and 68, respectively, is provided automatically in response to pivotal movement of the table frame 28 on the upper base 24. This movement is accomplished by pairs of cam and cam follower assemblies, each of which comprises an axe-head shaped cam member 76 and a cam follower 78 in the form of a roller journalled on a cap screw axle 82 intermediate the ends of the lower link 68. Each cam includes a generally horizontally extending, concave upper cam surface 76a and an outwardly convex, generally downwardly extending, forward cam surface 76b intersecting the upper cam surface at a point closely adjacent the foot end of the upstanding side frame portions 24a as best shown in FIGS. 3A and 3B. Each cam 76 is mounted on the inside surface of the adjacent side frame member portion 24a on a pair of spaced apart cap screw axle members 80 which are threaded into bosses 24b FIG. 4 provided on the inside face of the side frame members 24a. Each cam is adjustably mounted for limited travel along a generally horizontal axis defined between the spaced cap screws 80 which project through pairs of elongated slots 76c provided in each cam as shown in FIGS. 2, 3A and 3B.

Referring now to FIGS. 3A and 3B, as the table frame 28 is pivoted in a clockwise direction indicated by the arrow "F" from an upstanding position downwardly towards a horizontal position the cam follower rollers 78 ride forwardly (arrow "F" FIG. 3A) on the upper surfaces 76a of the cams 76 and thus limit downward travel of the lower ends of the lower links 68 as the table pivots downwardly. This arrangement provides for a relatively constant horizontal alignment during initial upward travel of the foot board 40 (arrows "J" FIG. 3A) as the table begins to ride upwardly while the plane "A" coincident with the patient supporting surface of the cushions 30 begins to rotate in a clockwise direction. As this occurs, the patient leans forwardly and the cushions accept the body weight of a patient originally standing on the platform.

The concave upper cam surfaces 76a are generally aligned along a common horizontal axis that is parallel to and spaced below these upper cam surfaces. The forward cam surfaces 76b intersect this axis generally transversely at a slope generally parallel with the foot end of the upstanding portions 24a of the side frame members 24. The uniquely shaped cam surfaces 76a and 76b provide for a generally parallel movement of the foot board 40 in an upward direction initially as the table frame 28 begins to pivot downwardly from the upstanding position of FIG. 3A. This action continues until the cam rollers 78 reach the upper end of the forward cam surfaces 76b and thereafter when the cam rollers begin to move downwardly while in contact with the forward cam surfaces 76b, the footboard 40 begins to pivot in a clockwise direction toward a near vertical tuck-away position when the patient's body weight is supported on the upper plane "A" of the cushions 30 as the table approaches the horizontal position.

The cams 76 are supported from the side frame portions 24a for limited horizontal adjustment of position thereon by virtue of the elongated slots 76c and the cams are adjusted so that during initial travel of the cam roller 78 upwardly, as indicated by the arrow "G" FIG. 3B, the lower links 68 pivot in a clockwise direction around the upper end pivot cap screws 70 so that the footboard 40 rapidly begin to pivot outwardly from the tuck-away position as indicated by the arrow "H" (FIG. 3B) during initial movement of the table frame 28 out of the horizontal position and upwardly toward the upstanding position as indicated by the arrow "C" (FIG. 3B). This action ensures that the upper surface pad 42 of the footboard 40 moves outwardly in order to be ready to receive the soles of the patient's feet as the table continues to pivot upwardly, and thus the automatically controlled footboard prevents the possibility of a patient sliding off of the foot end of the table as the table pivots toward the upstanding position.

When the cam rollers 78 reach the apex or intersection between the upper cam surfaces 76a and the forward cam 76b continued further pivotal movement of the table frame 28 in a counterclockwise direction results in travel of the cam rollers 78 inwardly along the upper cam surfaces 76a in a direction opposite to the arrows "I" in FIG. 3A. During this travel, the footboard 40 is maintained in a generally horizontal position (as illustrated in FIGS. 1 and FIGS. 3A) and moves in a downward direction opposite the arrows "J" until the table frame 28 reaches the maximum upright position as illustrated in FIG. 3A with the plane "A" of the upper surface of the cushions 30 extending upwardly at an angle "B" from the upper surface pad 42 on the footboard. The patient 12 then can conveniently step "onto" or "off of" the footboard which is at a level closely adjacent the floor surface 14.

Although the present invention has been described with reference to a single illustrated embodiment thereof, it should be understood that numerous other modifications and embodiments can be made by those skilled in the art that will fall within the spirit and scope of the principles of this invention.

What is claimed as new and is desired to be secured by Letters Patent is:

1. A patient treatment table, comprising:

base means adapted to be supported from a floor surface;

patient supporting table means having a patient support surface and a foot end surface, said table means mounted for pivotal movement relative to said base means between a generally horizontal position for patient treatment wherein said patient support surface is generally horizontal and a generally upstanding position wherein said patient support surface is extended upwardly for enabling a patient to mount and dismount more easily;

footboard means adjacent a foot end of said table means and having a foot support surface, an underside parallel thereof and an outer end, said footboard means mounted for movement between a generally horizontal position wherein said underside is near said floor surface and said outer end is projecting outwardly of an extension of said patient support surface of said table means for supporting a patient when said table means is in said upstanding position and a second position wherein said outer end of said footboard means is spaced beneath said foot end surface of said table means whensaid table means is in said horizontal position and wherein said underside of said footboard means is spaced inwardly toward said base means from the feet of a patient lying on said table means to provide unobstructed exposure of said patient's feet for treatment by a person standing on said floor surface outwardly of said foot end of said table means; and linkage means interconnecting said table means and said footboard means for moving said footboard means between said first and second positions as said table means is pivoted relative to said base means.

2. The patient treatment table of claim 1 wherein said linkage means includes adjustment means for adjusting the angle between said foot support surface of said footboard means and said patient support surface of said table means when said table means is in said upstanding position.

3. The patient treatment table of claim 1 wherein said linkage means includes means for pivoting said footboard means to move outwardly of and below the soles of the overhanging feet of a patient as said table means is moved from said horizontal position toward said upstanding position.

4. The patient treatment table of claim 3 wherein said outer end of said footboard means is movable from a position below said patient support surface of said table means when said table means is in said horizontal position to a position above an extension of said patient support surface as said table means is pivoted toward said upstanding position thereby to support the feet of a patient for dismounting from said table means when said table means begins to pivot toward said upstanding position.

5. The patient treatment table of claim 1 wherein said underside of said footboard means is generally parallel to said floor surface when said table means is in said upstanding position and is movable to a position generally normal to the patient support surface of said table means when said table means is in said horizontal position.

6. The patient treatment table of claim 5 wherein said table means includes cushion means having an end surface defining said foot end surface of said table means, and said underside of said footboard means is generally aligned with said end surface of said cushion means when said table means is in said horizontal position.

7. The patient treatment table of claim 1 wherein said linkage means includes first and second links having opposite ends pivotally interconnected between said table means and said footboard means, respectively, and first means supported from said base means for effecting relative pivotal movement between said first and second links as said table means pivots relative to said base means.

8. The patient treatment table of claim 7 wherein said first means comprises cam and cam follower means interacting between said base means and one of said first and second links to pivot said one link relative to the other as said table means pivots relative to said base means.

9. The patient treatment table of claim 8 wherein said cam and cam follower means includes a cam with first and second cam surfaces engaged by a cam follower, said first and second cam surfaces being positioned generally at right angles to each other.

10. The patient treatment table of claim 8 wherein said cam is supported from said base means and said cam follower is supported from said one link intermediate said opposite ends thereof.

11. The patient treatment table of claim 9 wherein said first cam surface is shaped to effect relatively slow pivotal movement of said footboard means out of said generally horizontal first position toward said second position as said table means is initially pivoted from said upstanding position toward said horizontal position until said cam follower closely approaches said second cam surface.

12. The patient treatment table of claim 11 wherein said second cam surface is shaped to effect pivotal movement of said footboard means to said second position as said cam follower moves from said first cam surface onto said second cam surface.

13. The patient treatment table of claim 12 wherein said cam follower comprises a roller mounted on said one link intermediate said opposite ends thereof in moving supported engagement above said first cam surface as said table means is pivoted from said upstanding position toward said horizontal position.

14. The patient treatment table of claim 13 wherein said second cam surface angularly intersects said first cam surface and is engageable with said roller upon downward travel thereof as said table mean continues said pivotal movement away from said upstanding position to reach said horizontal position.

15. The patient treatment table of claim 14 wherein said cam is mounted for reciprocal sliding movement relative to said base means along an axis generally aligned along the path of travel of said cam roller while engaged with said first cam surface.

* * * * *